US007648681B2

(12) United States Patent
Meyer et al.

(10) Patent No.: US 7,648,681 B2
(45) Date of Patent: Jan. 19, 2010

(54) SPECIMEN COLLECTION SYSTEM

(75) Inventors: Kevin Jon Meyer, Cincinnati, OH (US);
Betty Jo Smith, Batavia, OH (US)

(73) Assignee: Meridian Bioscience, Inc., Cincinnati, OH (US)

( * ) Notice: Subject to any disclaimer, the term of this patent is extended or adjusted under 35 U.S.C. 154(b) by 849 days.

(21) Appl. No.: 11/001,623

(22) Filed: Dec. 1, 2004

(65) Prior Publication Data

US 2006/0115385 A1    Jun. 1, 2006

(51) Int. Cl.
*B01L 3/00* (2006.01)
(52) U.S. Cl. .................. 422/102; 422/58; 422/104; 49/146; 49/162; 49/177; 222/557
(58) Field of Classification Search ............. 422/58, 422/102, 104; 600/562; 222/557; 49/146, 49/162, 177
See application file for complete search history.

(56) References Cited

U.S. PATENT DOCUMENTS

| 2,039,145 | A | * | 4/1936 | Burns | 222/545 |
| 3,516,581 | A | * | 6/1970 | Micallef | 222/529 |
| 4,225,423 | A | | 9/1980 | Cotey | |
| 4,559,837 | A | | 12/1985 | Cerqueira | |
| 4,742,928 | A | | 5/1988 | Braun | |
| 4,776,501 | A | | 10/1988 | Ostrowsky | |
| 4,805,790 | A | | 2/1989 | Leonetti | |
| 4,842,826 | A | * | 6/1989 | Guala | 422/102 |
| 5,036,889 | A | | 8/1991 | Pherigo | |
| 5,149,506 | A | | 9/1992 | Skiba | |
| 5,348,201 | A | | 9/1994 | Koo | |
| 5,381,914 | A | | 1/1995 | Koyama | |

(Continued)

FOREIGN PATENT DOCUMENTS

JP    5093722    4/1993

(Continued)

OTHER PUBLICATIONS

Meridian Diagnostics, Inc., Parasitology Products for the collection, transport and examination of fecal specimens, Dec. 1998, Cincinnati, Ohio.

(Continued)

*Primary Examiner*—Lyle Alexander
*Assistant Examiner*—Dennis M White
(74) *Attorney, Agent, or Firm*—Wood, Herron & Evans, LLP

(57) ABSTRACT

A system for collecting, transporting and preparing a fecal specimen for examination includes a container, a closure selectively secured over an open end of the container, and a sample collection member coupled to the closure and extending into the container when the closure is secured thereto. In one embodiment, the closure includes a base and a cap that are hingedly coupled together. The cap is selectively moveable between a closed position that seals an aperture in the base, and an open position wherein the aperture is exposed to permit expelling contents of the container through the aperture. In another embodiment, the closure comprises a base having a spout and an aperture, and a cap coupled to the base for axial movement along the spout between open and closed positions. The system may further include a deodorant to mask or absorb odors.

20 Claims, 6 Drawing Sheets

U.S. PATENT DOCUMENTS

| | | | |
|---|---|---|---|
| 5,385,259 A | | 1/1995 | Bernstein |
| 5,417,350 A | | 5/1995 | Koo |
| 5,440,942 A | * | 8/1995 | Hubbard .................. 73/864.91 |
| 5,503,309 A | | 4/1996 | Oder et al. |
| 5,542,557 A | | 8/1996 | Koyama |
| 5,577,625 A | | 11/1996 | Baird |
| 5,624,554 A | * | 4/1997 | Faulkner et al. ............. 210/232 |
| 5,744,082 A | | 4/1998 | Bak |
| 5,906,841 A | | 5/1999 | Bak |
| 6,253,937 B1 | | 7/2001 | Anderson |
| 6,530,493 B2 | | 3/2003 | Anderson |
| 6,596,502 B2 | | 7/2003 | Lee |
| 2005/0196318 A1 | * | 9/2005 | Matusewicz et al. .......... 422/58 |

FOREIGN PATENT DOCUMENTS

| | | |
|---|---|---|
| JP | 6317583 | 11/1994 |
| JP | 6331623 | 12/1994 |
| JP | 7012808 | 1/1995 |
| JP | 8292189 | 11/1996 |
| JP | 9292392 | 11/1997 |
| JP | 10160728 | 6/1998 |
| JP | 10260116 | 9/1998 |
| JP | 11064331 | 3/1999 |
| JP | 11295194 | 10/1999 |
| JP | 11316222 | 11/1999 |
| JP | 2000338102 | 12/2000 |
| JP | 2001099763 | 7/2001 |
| JP | 2002131311 | 5/2002 |
| JP | 2002148257 | 5/2002 |
| JP | 2002207033 | 7/2002 |

OTHER PUBLICATIONS

Meridian Diagnostics, Inc., Ultra Revolutionary Design Makes Parasitology Faster and Easier; Nov. 1996, Cincinnati, Ohio.

* cited by examiner

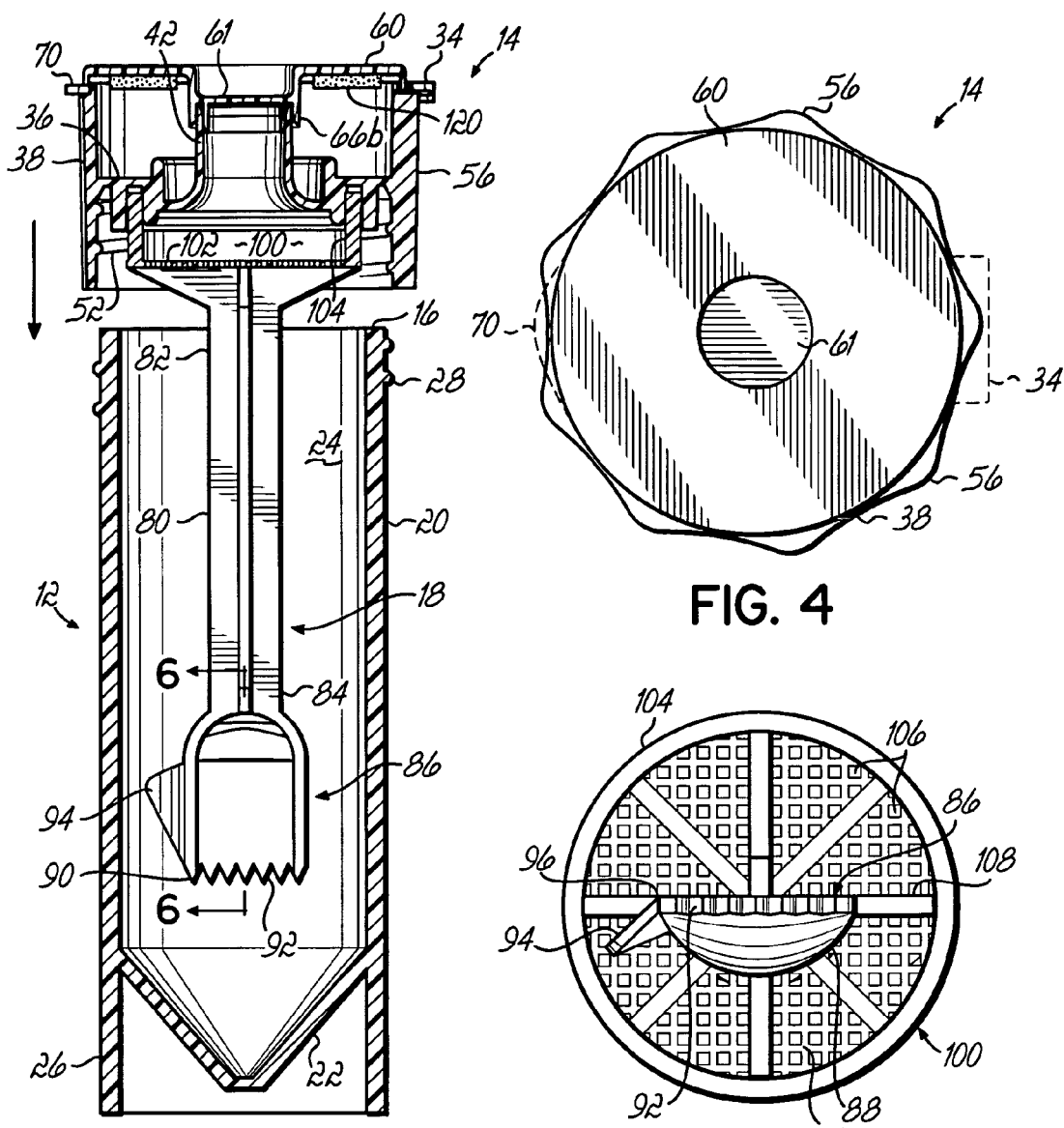
FIG. 4
FIG. 5
FIG. 2
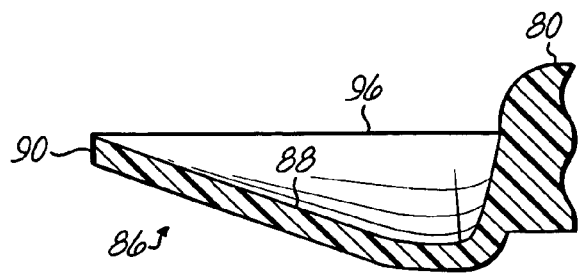
FIG. 6

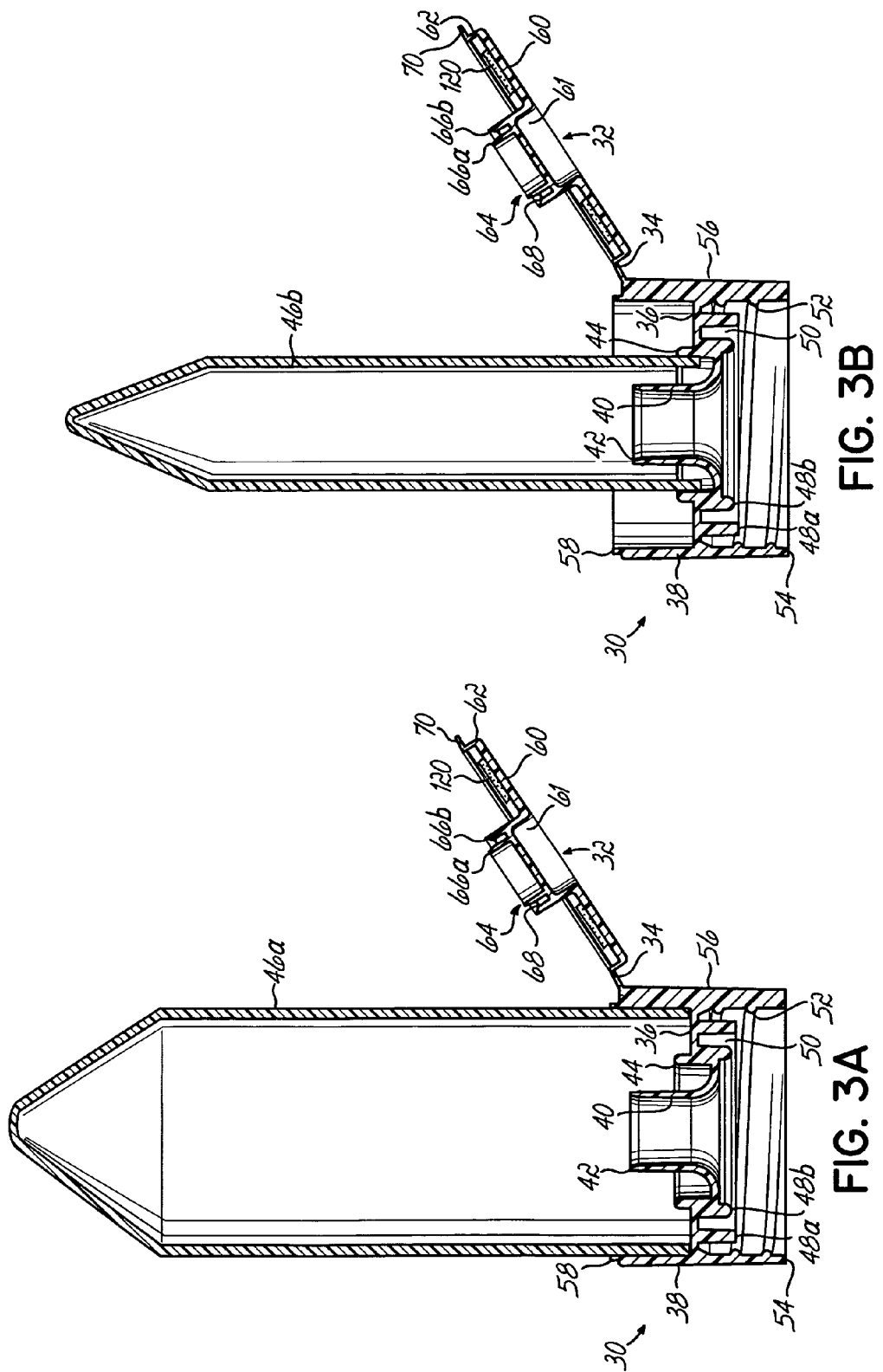

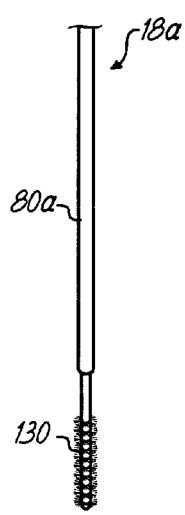 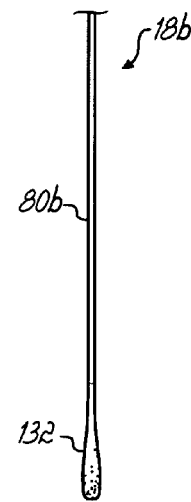 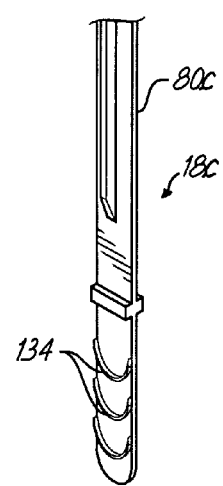 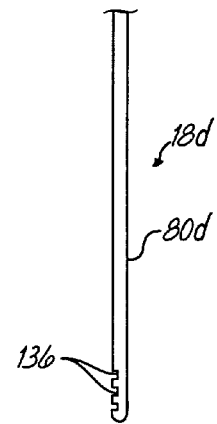
FIG. 9A   FIG. 9B   FIG. 9C   FIG. 9D
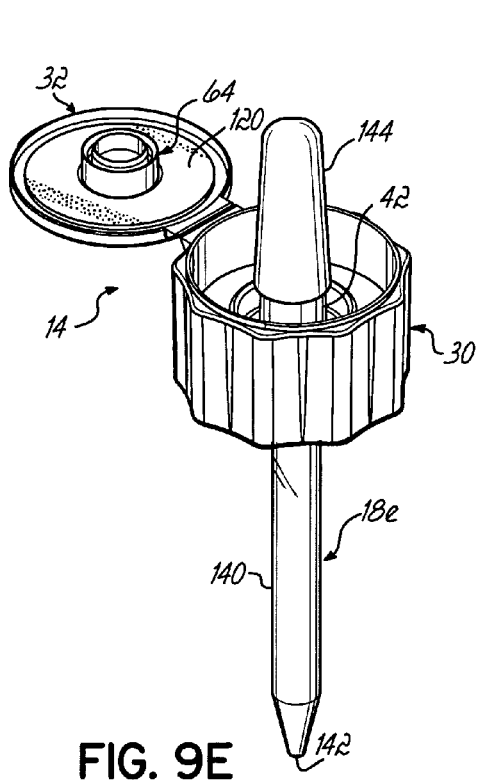 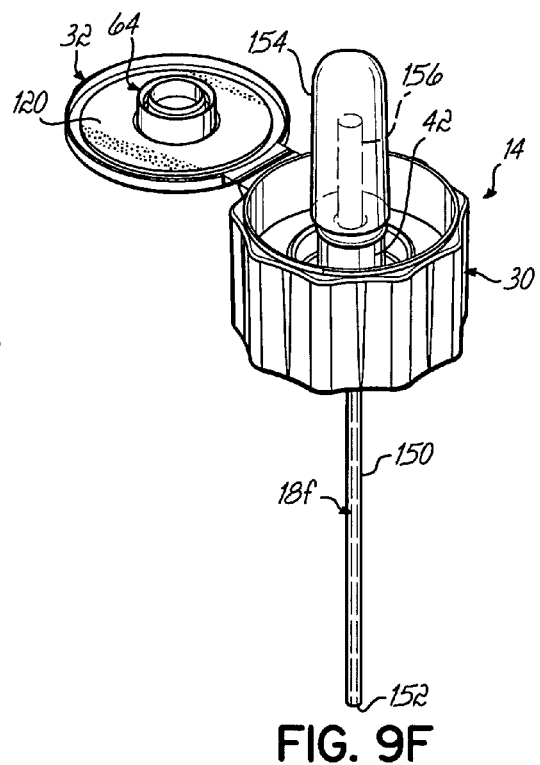
FIG. 9E   FIG. 9F

SPECIMEN COLLECTION SYSTEM

FIELD OF THE INVENTION

The present invention relates generally to specimen collection devices, and more particularly to devices for collecting, transporting and preparing specimens for examination.

BACKGROUND OF THE INVENTION

Many devices are available for collecting, transporting and preparing specimens for examination. For example, during the diagnosis and treatment of diseases and illnesses in humans and animals, it is often necessary to collect and analyze fecal specimens. Prior fecal specimen collection devices typically include a container with a screw-type lid or other closure that requires manipulation by both hands of a user to open and close the container. Many such collection devices also include a spoon or similar implement to facilitate separating a portion of the fecal matter and placing it within the container. Some of these prior collection spoons are prone to allowing some of the collected specimen to inadvertently contact the user if the user is not careful during the handling and placement of the fecal specimen within the container.

The container usually contains a fixative to reduce the effects of delay between the collection and subsequent analysis of the fecal specimen. After collection, reagents may be added to the container to facilitate preparation of the specimen for examination. As a consequence of containing fecal matter and various chemicals mentioned above to preserve and prepare the fecal specimen, technicians and others who process the fecal specimen are often exposed to objectionable odors.

It is often necessary to transfer at least some of the contents of the container to another container or vial for further processes. During such handling, it is desired to avoid or minimize exposure of the specimen to technicians or others handling the collection device. Accordingly, closures for fecal collection devices are typically configured to seal contents placed within their containers in a leak-free manner. While they may be effective in providing leak-free seals, these prior closures are typically cumbersome for technicians to handle, often requiring both hands to manipulate the closure. Moreover, these prior closures are unwieldy to manipulate while wearing protective gloves. A need therefore exists for a fecal specimen collection and transport system that overcomes these and other drawbacks.

SUMMARY OF THE INVENTION

The present invention provides a specimen collection and transport system that facilitates collecting and preparing a specimen, and that minimizes exposure of the specimen and odors of the specimen and reagents to persons handling the specimen. In one embodiment, the collection system includes a container for receiving the specimen. The container has an open end with external threads and an interior reservoir. A closure is removably coupled to the container and comprises a base and a cap pivotally coupled to the base. The cap is configured so that it can be manipulated with one hand of a user, such as by using a thumb, to move the cap between a closed position in which a seal on the cap engages an aperture in the base to prevent the contents of the container from passing through the aperture, and an open position wherein the contents of the container are exposed and may be expelled through the aperture. The closure may be, for example, a flip-top type closure or a toggle-type closure.

In another embodiment, the closure comprises a base having a spout and an aperture communicating with the interior reservoir of the container. A cap is coupled to the base and is axially moveable along the spout between a closed position where a seal on the cap engages the aperture to prevent communication between the reservoir and the environment, and an open position where the contents of the reservoir may be expelled through the aperture.

The specimen collection system further includes a sample collection member extending from the base of the closure. The sample collection member is disposed in the reservoir of the container when the closure is coupled to the open end. When it is desired to obtain a sample of a specimen, such as a fecal specimen for example, the closure is removed from the container and the sample collection member is used to divide the fecal specimen and remove a portion of the fecal specimen for placement in the container.

In one embodiment, the sample collection member includes an elongate shaft having a scoop at one end to facilitate collecting a sample. The other end of the shaft is coupled to the base of the closure. The scoop has an arcuate bottom wall and a serrated edge to facilitate obtaining a sample of the fecal specimen. In another embodiment, the scoop further includes an inclined surface extending outwardly and downwardly from an upper edge of the scoop to facilitate dividing the fecal specimen and obtaining a sample. In yet another embodiment, the bottom wall of the scoop deepens in a direction from the distal edge of the scoop toward the shaft to ensure that the sample is retained on the scoop when the shaft is maintained in a substantially horizontal position.

In another embodiment, the sample collection system further includes a filter adjacent the aperture to facilitate the preparation and dispensing of liquid material from the container for analysis.

In yet another embodiment, the sample collection system includes a tubular spout extending upwardly from the base of the closure to define the aperture. The closure further includes a tubular projection formed in the base and extending upwardly from the base around the aperture. The closure also includes at least one sidewall extending upwardly from the base, generally surrounding the spout and tubular projection. The different sizes of the sidewall the tubular projection permit differently sized vials to be sealingly engaged with the sidewall or tubular projection to facilitate transferring the contents of the reservoir through the aperture to the vials. The sidewalls of the container may be pliable to facilitate expelling the contents of the reservoir through the aperture.

In another embodiment, a method of preparing a specimen includes one-handed opening of a closure of a sample collection system and expelling at least some of the contents of a reservoir of the sample collection system through an aperture in the closure.

These and other embodiments of the invention will become more readily apparent to those of ordinary skill in the art upon review of the following detailed description taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to further explain the invention.

FIG. 2 is a cross-sectional view of the fecal collection system of FIG. 1 with the closure removed from the container;

FIGS. 3A-3B are cross-sectional views of the closure of FIG. 2 depicting use of the closure with differently sized vials coupled to the closure;

FIG. 4 is a top plan view of the closure of FIG. 1;

FIG. 5 is an end view of a sample collection member;

FIG. 6 is a partial cross-sectional view of the sample collection member of FIG. 2, taken along line 6-6;

FIGS. 9A-9D are partial perspective views depicting additional embodiments of sample collection members according to the invention;

FIG. 9E is a perspective view of a closure and sample collection member in the form of a dropper, according to another embodiment of the invention;

FIG. 9F is a perspective view of a closure and sample collection member according to yet another embodiment of the invention.

DETAILED DESCRIPTION

Figure 1:
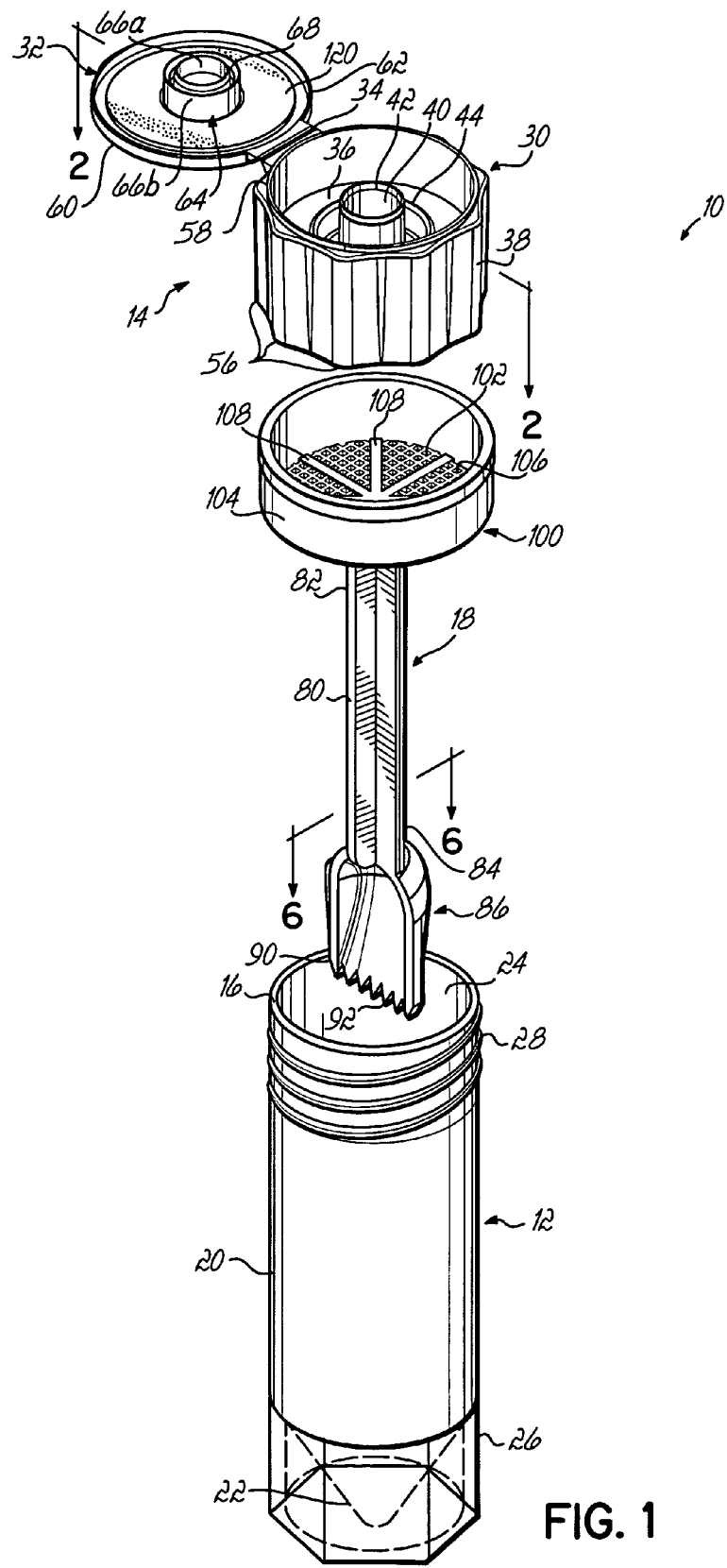
FIG. 1 is an exploded perspective view of an exemplary fecal specimen collection and transport system according to the present invention.

Referring to FIG. 1, there is shown an exemplary specimen collection and transport system 10 according to the present invention. The collection and transport system 10 includes a container 12, a closure 14 selectively removably coupled to the container 12 proximate an open end 16 thereof, and a sample collection member 18 coupled to the closure 14 and disposed within the container 12 when the closure 14 is coupled to the open end 16 of the container 12. With continued reference to FIG. 1, and referring further to FIG. 2, the exemplary container 12 has a generally tubular shape defined by an elongate sidewall 20 extending from the first, open end 16 to a second, closed end 22. The sidewall 20 defines an interior reservoir 24 of the container 12, accessible through the first, open end 16. In the embodiment shown, the second, closed end 22 of the container 12 has a generally conical shape for accommodating the sample collection member 18, as will be described in more detail below. A circumferential skirt 26 extends from the second end 22 of the container 12 and surrounds the conically shaped portion. The skirt 26 is formed with a series of circumferentially extending flat surfaces in a generally octagonal formation to facilitate grasping the container 12.

The container 12 is formed from polymeric material and, in one embodiment, it is transparent, or at least translucent, so the contents of the container 12 may be observed through the sidewall 20. The sidewall 20 of the container is flexible to facilitate expelling the contents of the container 12 when the sidewall 20 is squeezed by a user. External screw threads 28 are provided at the first end 16 of the container 12, proximate the opening, to facilitate threaded engagement of the closure 14 with the open end of the container 12. While the container 12 is depicted as having a generally tubular shape described above, it will be recognized that the container may have various other configurations suitable for receiving a sample of a specimen, such as a fecal specimen for example, and a closure to secure the sample therein.

In one embodiment, the closure 14 comprises a base 30 and a cap 32 that are hingedly coupled together via a living hinge 34 formed between respective peripheral edges of the base 30 and cap 32 for movement between an open position, depicted in FIG. 1, and a closed position, depicted in FIG. 2. The base 30 of the closure 14 includes an end wall 36 and a generally circular sidewall 38. An aperture 40 is formed through the end wall 36 and communicates with the interior reservoir 24 of the container 12 when the closure 14 is secured over the open end 16 of the container 12. While the hinge 34 is depicted herein as a living hinge integrally formed with the base 30 and cap 32, it will be recognized that other configurations may be used to facilitate coupling the cap 32 to the base 30 while retaining the cap 32 in close proximity to the base 30 for quick and easy replacement of the cap 32 in the closed position. For example, the cap 32 may be coupled to the base 30 by a tether, or it may be coupled to the base 30 for pivotal movement about an axis generally perpendicular to the end wall 36, or by any other method suitable to facilitate replacement of the cap 32 to the closed position.

In use, additives such as reagents, preservatives, fixatives, etc. may be added to the container 12 through the aperture 40, and the contents of the container 12 may be expelled through the aperture 40 as may be desired. In the embodiment shown, the aperture 40 is defined by a generally tubular spout 42 projecting upwardly from the end wall 36. The spout 42 is located centrally on the end wall 36 and is generally concentric with the sidewalls 38 of the base. It will be recognized, however, that spout 42 may alternatively be located eccentrically with respect to the end wall 36 and sidewalls 38. The base 30 further includes a tubular projection 44 positioned concentrically around the spout 42 and extending upwardly from the end wall 36. The inner diameters of the tubular projection 44 and the sidewall 38 of base 30 are sized to provide interference fits with the outer diameters of differently sized vials 46a, 46b, as depicted in FIGS. 3A and 3B, such that fluid tight seals are formed between the base 30 and the vials 46a, 46b, to facilitate transferring the contents of the interior reservoir 24 to the vials for further processing and analysis.

With continued reference to FIGS. 3A and 3B, two concentric projections 48a, 48b extend downwardly from the end wall 36 of the base 30, in a direction opposite the cap 32, and define an annular space 50 therebetween for receiving the first end of the sample collection member 18, as depicted in FIG. 2. The sidewall 38 of the base 30 includes interior threads 52 formed thereon and extending from the lower edge 54 of the sidewall 38 toward the end wall 36 of the base, such that the closure 14 may be threadably secured to the open end 16 of the container 12. It will be recognized, however, that closure 14 may have various other configurations for securing closure 14 to the open end 16 of the container 12. For example, closure 14 may be configured to be secured to the open end 16 by a snap-fit type arrangement, by an interference fit between the closure 14 and the open end 16, or by any other method or configuration suitable for securing closure 14 to the open end 16 of the container 12.

As depicted in FIG. 2, the sample collection member 18 extends into the reservoir 24 of the container 12 when the closure 14 is secured to the container 12, as described above. As best depicted in FIG. 4, the outer surface of the sidewall 38 of the base 30 may include a plurality of spaced arcuate projections 56 extending radially outwardly from the sidewall 38 to facilitate gripping the closure 14 when it is desired to secure the closure onto, or remove the closure from, the container 12. The spaced arcuate projections 56 ensure a firm grip on the closure 12 even when users are wearing protective gloves. In the embodiment shown, the sidewalls 38, the end wall 36, the spout 42, and the projections 44, 48a, 48b on the base 30 may be formed with substantially the same wall thickness to facilitate injection molding of the base portion of the closure 12. A raised rim 58 is formed on an end of the sidewall 38, adjacent hinge 34 to facilitate securing the cap 30 in the closed position.

Referring now to FIGS. 1-4, the cap 32 of the closure 12 comprises a top wall 60 which may have a generally circular shape, and a sidewall 62 extending perpendicularly from the top wall 60 proximate a peripheral edge thereof. The sidewall 62 frictionally engages raised rim 58 on base 30 to help retain cap 32 in the closed position. The top wall 60 is substantially flat, and has a central depression 61. A seal 64 is located generally centrally on the top wall 60 of the cap 32 for engaging the spout 42 on the base 30 when the cap 32 is placed in the closed position. The seal 64 comprises a pair of concentric tubular projections 66a, 66b extending from the top wall 60 of the cap 32 to define an annular space 68 between the tubular projections 66a, 66b for receiving the upper edge of the spout 42 when the cap 32 is in the closed position. The dimensions and spacing of the concentric projections 66a, 66b are selected such that a fluid tight seal is formed between the concentric tubular projections and the spout 42, as depicted in FIG. 2. While the seal 64 is shown and described in this embodiment as being generally centrally located on top wall 60, and having concentric tubular projections 66a, 66b, it will be recognized that seal 64 may alternatively be located eccentrically on top wall 60, to correspond to an eccentrically located spout 42, and may have various other configurations suitable for sealing aperture 40.

In one embodiment, the cap 32 further includes a lip 70 extending radially outwardly from the peripheral edge of the top wall 60. The lip 70 is positioned relative to the spaced arcuate projections 56 on the sidewall 38 of the base 30, and is disposed generally opposite the hinged interface between the cap 32 and the base 30 to facilitate dislodging the cap 32 from the closed position and moving it toward the open position. In this manner, the cap 32 may be moved from the closed position to the open position to thereby provide communication between the reservoir 24 of the container 12 and the environment, through the aperture 40, by using only the fingers of one hand, such as a thumb. In particular, a user can engage the lip 70 on the cap 32 with his or her thumb while holding the container 12 with the palm and remaining fingers of that hand to thereby flip the cap 32 from the closed position toward the open position.

Figure 7A:
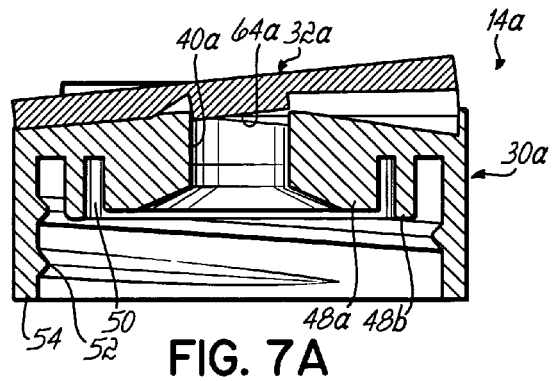
FIG. 7A is a cross-sectional view of a second embodiment of a closure according to the invention, depicted in an open configuration.
Figure 7B:
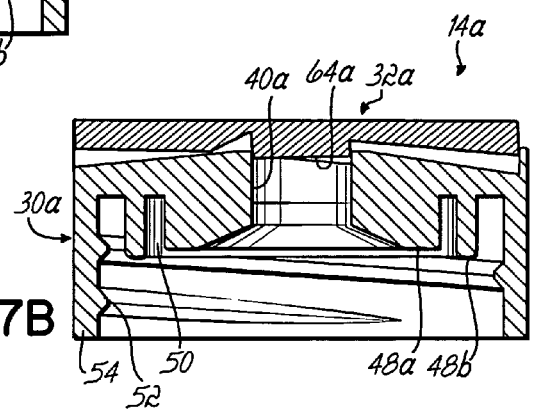
FIG. 7B is a cross-sectional view of the closure of FIG. 7A, depicted in a closed configuration.

Referring now to FIGS. 7A and 7B, another embodiment of a closure 14a according to the invention includes a cap 32a coupled to a base 30b for pivotal movement between an open position (FIG. 7A) and a closed position (FIG. 7B). This type of closure configuration is commonly referred to as a "toggle" closure. In this embodiment, a seal 64a on the cap 32a plugs an aperture 40a formed in the base 30a when the cap 32a is in the closed position. To move the cap 32a to the open position, one edge of the cap 32a is depressed, for example, with the thumb or finger of a user, to pivot the cap 32a, thereby raising the seal 64a away from the aperture 40a and permitting the contents of the reservoir 24 of the container 12 to be expelled through aperture 40a.

Figure 8A:
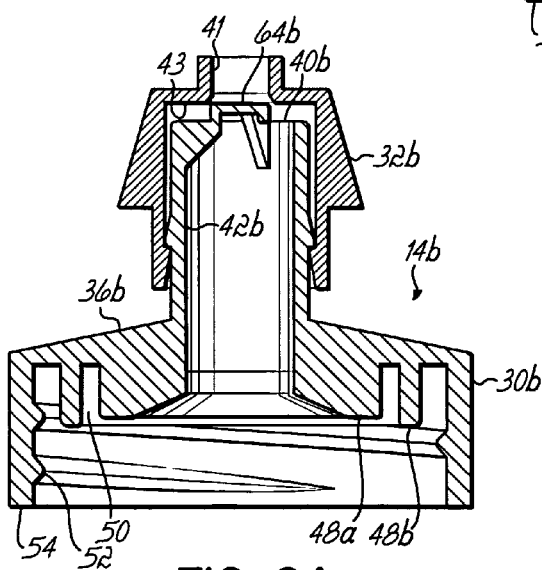
FIG. 8A is a cross-sectional view of a third embodiment of a closure according to the invention, depicted in an open configuration.
Figure 8B:
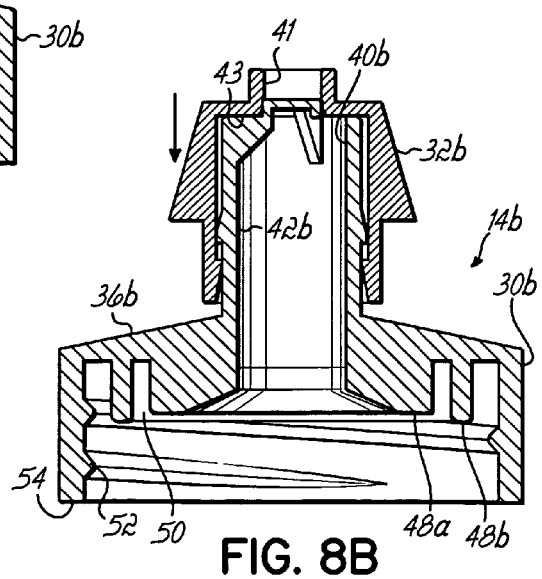
FIG. 8B is a cross-sectional view of the closure of FIG. 8A, depicted in a closed configuration.

In yet another embodiment depicted in FIGS. 8A and 8B, a closure 14b for the specimen collection and transport system 10 includes a base 30b with a generally tubular spout 42b extending upwardly from an end wall 36b. An aperture 40b formed at a distal end of the spout 42b communicates with the interior reservoir 24 of the container 12 to facilitate expelling the contents of the reservoir. The closure 14b further includes a cap 32b coupled to the spout 42b for axial movement therealong, between an open position depicted in FIG. 8A, and a closed position depicted in FIG. 8B. In the closed position, a seal 64b formed on the spout 42b, shown here in the form of a plug, engages an outlet 41 formed in the cap 32b, and an inner surface 43 of the cap 32b engages the aperture 40b to prevent the contents of the reservoir 24 from passing through the aperture 40b and outlet 41. When it is desired to expel at least some of the contents of the reservoir 24, to examine the fecal sample for example, the cap 32b may be moved from the closed position to the open position, whereby the seal 64b is disengaged from the outlet and the inner surface of the cap 32b moves away from the aperture 40b so that the contents of the reservoir 24 may pass through the outlet 41.

While closure 14b has been shown and described as having a seal 64b on the spout 42b of base 30b, it will be recognized that the seal may alternatively be provided on the cap 32b and may be configured to seal against corresponding features on the base 30b. Other features of the closure 14b, which are similar to those features of closures previously described, are numbered similarly.

Figure 10:
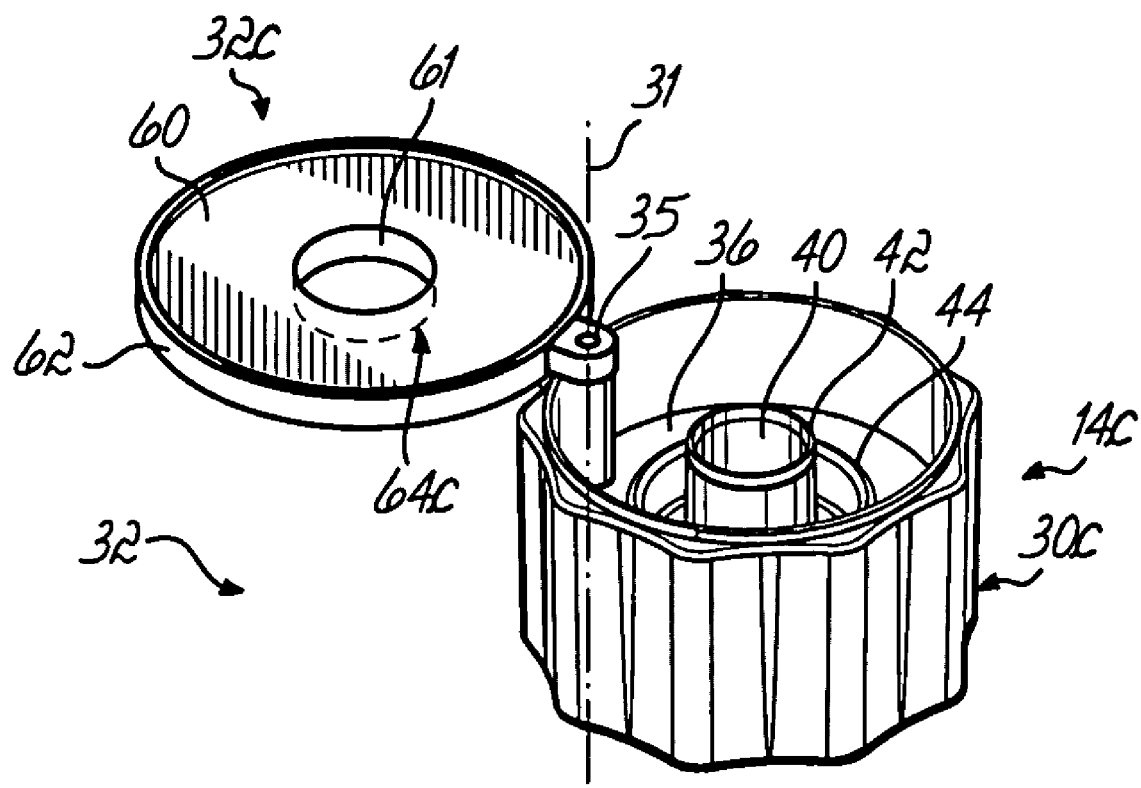
FIG. 10 is a perspective view of a fourth embodiment of a closure according to the invention.

FIG. 10 depicts yet another exemplary embodiment of a closure 14c according to the invention wherein cap 32c is coupled to base 30c for pivotal movement about an axis 31 which is generally perpendicular to end wall 36. In the embodiment shown, a hinge pin 35 formed into the cap 32c secures cap 32c for pivotal movement relative to base 30c between an open position wherein aperture 40 is exposed, and a closed position (not shown) wherein a seal 64c disposed on cap 32c sealingly engages tubular spout 42 and aperture 40. The closure 14c is similar in construction to closure 14 described above, and corresponding features have been similarly numbered.

Referring now to FIGS. 1, 2 and 5, one embodiment of a sample collection member 18 will now be described. The sample collection member 18 comprises an elongate shaft 80, a first end 82 of which is configured to be coupled to the base 30 of the closure 14. The second end 84 of the shaft 80 is provided with a scoop 86 that facilitates collecting a sample of a specimen such as fecal matter, for example, and placing the sample within the interior reservoir 24 of the container 12. In particular, the sample collection member 18 is withdrawn from the interior reservoir 24 of the container 12 when a user uncouples the closure 14 from the open end 16 of the container 12. Grasping the base 30 of the closure 14, a user is then able to obtain an appropriately sized sample of the specimen using the scoop 86 of the sample collection member 18 and place the sample within the interior reservoir 24 by inserting the shaft 80 into the interior reservoir 24 and securing the closure 14 to the open end 16 of the container 12.

As depicted in FIGS. 1, 5 and 6, the scoop 86 has a generally arcuate bottom wall 88 that deepens in a direction from a distal edge 90 of the scoop toward the shaft 80, such that a sample collected on the scoop 86 can easily be retained on the scoop while a user holds the sample collection member 18 with the shaft 80 in a substantially horizontal orientation. Because the user does not have to tilt the shaft 80 of the sample collection member 18 in a direction toward the closure 14, where the user is grasping the sample collection member 18, the possibility that the user will come in contact with the sample is minimized.

As best depicted in FIGS. 1 and 2, the distal end 90 of the scoop 86 includes serrations 92 formed thereon to facilitate separating the specimen to be collected and obtaining a sample of the specimen on the scoop. Because of this serrated configuration, in conjunction with the arcuate-shaped bottom wall 88, such sample collection members are frequently referred to as "sporks." To further facilitate obtaining a sample of the specimen, the scoop 86 includes an outwardly projecting surface 94 extending from a top edge 96 of the scoop 86, and inclined in a direction relatively downward from the top edge 96 of the scoop 86.

The exemplary sample collection member 18 shown further includes a filter 100 disposed adjacent the aperture 40 in the base 30 of the closure 14 to facilitate separating particulate matter from liquid preparations formed in the reservoir 24 of the container 12. In the embodiment shown, the filter 100 is provided on the first end 82 of the shaft 80 and includes a bottom wall 102 having a substantially circular shape and a sidewall 104 extending generally upwardly therefrom around a peripheral edge of the bottom wall 102. The bottom wall 102 includes a plurality of perforations 106 formed therethrough to permit liquid material to flow through the bottom wall 102 while prohibiting the passage of particulate matter larger than the size of the perforations 106. It will be recognized that the size of the perforations 106 may be selected to filter out particulate matter of any size, as may be desired. The bottom wall 102 of the filter 100 further includes a series of radially-extending ribs 108 to increase the strength of the perforated bottom wall 102. The bottom wall outer diameter, and the corresponding sidewall 104, is configured such that the sidewall 104 will be received within the annular space 50 formed between projections 48a, 48b of the base 30 of the closure 14, as described above, so that the sample collection member 18 may be securely attached to the base 30 of the closure 12.

The container 12, closure 14, and sample collection member 18 may all be formed from polymeric materials available from, for example, Biomedical Polymers, Inc. of Gardner, Mass. It will be recognized that any or all of these components may alternatively be formed from other materials suitable for collecting a specimen and preparing it for examination.

FIGS. 9A through 9F depict various other embodiments of sample collection members that could be used with the specimen collection system 10. These various embodiments may be used to facilitate the collection of different types of specimens, such as urine, sputum, saliva, blood, pustule discharge, water, and other liquids; viral, fungal, or bacterial specimens; samples of meat products (e.g. ground beef, pork, poultry), samples of dairy products (e.g. cheese, eggs), and other food products; hair, fingernails, blood cells, animal and plant tissue, or other organic materials or foreign bodies removed therefrom; or various other types of specimens. This list of various possible specimen types is non-exhaustive and is in no way intended to limit the various types of sample collection members that could be incorporated into the specimen collection system 10.

FIG. 9A depicts a sample collection member 18a comprising an elongate shaft 80a that may be coupled to the base 30 of the closure 14 in a manner similar to that shown and described above. A brush 130 is provided on a distal end of the shaft 80a to facilitate the collection of a specimen. FIG. 9B depicts a sample collection member 18b having an elongate shaft 80b with a swab 132 provided on its distal end. FIG. 9C depicts a sample collection member 18c having a generally thin, flat, spatula-like shaft 80c. Several arcuate projections 134 extend from a lateral surface of the shaft 80c to facilitate retaining a portion of a specimen on the shaft 80c when the sample collection member 18c is withdrawn after having been inserted into the specimen. FIG. 9D depicts a sample collection member 18d having an elongate shaft 80d with several notches or serrations 136 formed into its distal end to facilitate retaining a portion of a specimen on the shaft 80d, in a manner similar to sample collection member 18c.

The sample collection member may be configured to facilitate obtaining an appropriately sized sample of a specimen. For example, scoop 86 of sample collection member 18 may be sized to facilitate obtaining a desired sample quantity for placement into the container 12. Alternatively, projections 134, notches 136, or other features may be formed into the sample collection members 18, 18c, 18d to facilitate obtaining an appropriately sized sample of a specimen. These features may be used alone, or in combination with indicators on the container 12, to indicate a quantity or volume of a specimen sample that is appropriate for collection or for conducting experiments using the collected specimen.

FIG. 9E depicts another embodiment of a sample collection member 18e in the form of a dropper. The sample collection member 18e is coupled to closure 14 in a manner similar to that described above with respect to sample collection member 18, and comprises a hollow tube 140 having an open end 142 extending in a direction opposite the closure 14. Tubular spout 42 on the closure 14 is in fluid communication with hollow tube 140, and an aspirator, such as a flexible bulb 144, is removably coupled to the spout 42 after cap 32 has been moved to the open position. Once connected, the flexible bulb 144 can be squeezed by a user to draw liquid material into, or expel liquid material from the tube 140.

FIG. 9F depicts another embodiment of a sample collection member 18f coupled to closure 14. In this embodiment, sample collection member 18f comprises a narrow tube 150 having an open end 152 extending in a direction away from the closure 14. The hollow tube 150 can be used to obtain a liquid sample, for example, by capillary action. Although not required, a flexible bulb 154 may be removably coupled to spout 42, as described above with respect to sample collection member 18e, to be in fluid communication with the tube 150. The flexible bulb 154 may be used to facilitate obtaining a liquid sample, or may alternatively be provided with a reagent or fixative to be added to the collected specimen. The bulb 154 may be provided with an elongate, frangible plug 156 sealing an outlet of the bulb 154, to prevent communication between the bulb 154 and tube 150 until the plug 154 is manipulated and broken off by a user. In this manner, a reagent or fixative can be provided in the bulb 154 and kept separate from a collected specimen until it is desired to add the reagent or fixative to the collected specimen.

In one embodiment, the specimen collection and transport system 10 further includes a deodorant to eliminate, absorb or mask odors caused by the specimen, or produced by various chemicals that may be added to the container 12 to preserve or prepare the specimen for examination. As used herein, the term, deodorant, is intended to include both materials that produce odors to mask or cover up odors of the specimen or chemicals (odorants), and materials that absorb or otherwise reduce or eliminate odors, such as charcoal or other materials. In the embodiment shown in FIGS. 1 and 2, the deodorant is provided as an insert 120 that is secured to the inner surface of the top wall 60 of the cap 32. The insert 120 may be secured to the cap 32, for example, by an adhesive, or by sizing the insert 120 to create an interference fit with features of the cap 32 such that the insert 120 is frictionally retained thereon. In another embodiment, the deodorant is integrally formed with the container 12, the closure 14, or both, by adding deodorant materials to the polymers used to form the container 12 and/or closure 14. It will be recognized that a deodorant can be included in the specimen collection and transport system 10 in various other ways, so long as the deodorant does not adversely affect examination of the specimen.

The specimen collection and transport system 10 may further include tamper-indicating features configured to indicate when the closure 14 has been opened after a sample has been collected. For example, the system may include a shrink wrap seal or tamper-indicating tape that may be applied to cover the container 12 and closure 14 after a sample has been collected and placed within the container 12. The specimen collection and transport system 10 may further include indicia, in the form of a label, or provided on the tamper indicating features, that provide instructions for using the system.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be made from such details without departing from the scope or spirit of the general inventive concept.

What is claimed is:

1. A specimen collection system, comprising:
   a container having an open end and an interior reservoir;
   a closure removably coupled to said container proximate said open end, said closure comprising:
      a base,
         a cap pivotally coupled to said base and movable between a closed position and an open position,
         said base including an aperture therethrough for communication between said reservoir and the environment when said cap is in said open position,
         said cap including a seal selectively engaging said aperture when said cap is in said closed position and thereby preventing communication between said reservoir and the environment in said closed position; and
      a sample collection member extending from said base of said closure and disposed in said reservoir of said container when said closure is coupled to said open end of said container;
   wherein said sample collection member comprises an elongate shaft having first and second ends, said first end coupled to said base of said closure, said second end including a scoop to facilitate collecting a sample, said scoop having an arcuate bottom wall and a serrated distal edge;
   wherein said scoop has an upper edge and wherein said sample collection member further comprises an inclined surface extending externally of said scoop in a direction outwardly and downwardly from said upper edge; and
   wherein said inclined surface intersects said scoop continuously along said upper edge.

2. The system of claim 1, wherein said cap is pivotally coupled to said base by a hinge.

3. The system of claim 1, wherein said base comprises a bottom wall and said cap is coupled to said base for pivotal movement about an axis substantially perpendicular to said bottom wall.

4. The system of claim 1, wherein said bottom wall of said scoop deepens in a direction from said distal edge toward said shaft to facilitate retaining a sample thereon while said shaft is maintained in a substantially horizontal orientation.

5. The system of claim 1, wherein said first end of said shaft is removably coupled to said base of said closure.

6. The system of claim 1, further comprising a filter disposed adjacent said aperture through said base, such that liquid expelled from said reservoir through said aperture passes through said filter.

7. The system of claim 6, wherein said filter is on said first end of said shaft of said sample collection member.

8. The system of claim 1, wherein said closure is a toggle-type closure.

9. The system of claim 1, wherein said closure includes a plurality of spaced arcuate projections extending radially outwardly from a peripheral edge of said base to facilitate gripping said closure for ease of threadably coupling said closure to, and uncoupling said closure from, said container.

10. The system of claim 1, wherein said closure further comprises a lip extending radially outwardly from said cap, beyond an outer peripheral edge of said base when said cap is in said closed position, such that said cap can be moved from said closed position to said open position by manipulation of said cap with the digits on a single hand of a user.

11. The system of claim 1, wherein said aperture is defined by a tubular spout extending from said base, and wherein said seal comprises concentric, tubular projections extending from said cap such that said spout is sealingly received within an annular space formed between said tubular projections.

12. The system of claim 1, wherein said base includes a bottom wall and at least one sidewall extending substantially perpendicularly from a peripheral edge of said bottom wall, said sidewall sized to sealingly engage an outer diameter of a vial to which contents of said reservoir are transferable through said aperture to the vial.

13. The system of claim 1, further comprising a tubular projection formed on said base of said closure, opposite said sample collection member and around said aperture, said tubular projection sized to sealingly engage an outer diameter of a vial to which contents of said reservoir are transferable through said aperture to the vial.

14. The system of claim 13, wherein said base includes a bottom wall and at least one sidewall extending substantially perpendicularly from a peripheral edge of said bottom wall, said sidewall sized to sealingly engage an outer diameter of a vial of a size different than the size of the vial engaged by said tubular projection formed on said base, whereby contents of said reservoir are transferable through said aperture to the vial.

15. The system of claim 1, further comprising a deodorant to mask or absorb odors produced by the contents of said reservoir.

16. The system of claim 15, wherein said deodorant is disposed on said closure.

17. The system of claim 15, wherein said deodorant is formed integrally with at least one of said closure and said container.

18. The system of claim 1, wherein said container comprises pliable sidewalls to facilitate expelling contents from said reservoir through said aperture.

19. The system of claim 1, wherein said arcuate shape of said bottom wall extends substantially between lateral edges of said scoop.

20. A specimen collection and transport system, comprising:
   a container having an open end and an interior reservoir;
   a closure removably coupled to said container proximate said open end, said closure comprising:
      a base having a generally tubular spout,
      a cap coupled to said base and movable axially along said spout between a closed position and an open position, an aperture in one of said base or said cap, said aperture providing a fluid path communicating with said interior reservoir, and the other of said base or said cap including a seal selectively engaging said aperture when said cap is in said closed position, thereby preventing communication between said reservoir and the environment in said closed position; and a sample collection member extending from said base of said closure and disposed in said reservoir of said container when said closure is coupled to said open end of said container;

wherein said sample collection member comprises an elongate shaft having first and second ends, said first end coupled to said base of said closure, said second end including a scoop to facilitate collecting a sample, said scoop having an arcuate bottom wall and a serrated distal edge;

wherein said scoop has an upper edge and wherein said sample collection member further comprises an inclined surface extending externally of said scoop in a direction outwardly and downwardly from said upper edge; and wherein said inclined surface intersects said scoop continuously along said upper edge.

* * * * *

UNITED STATES PATENT AND TRADEMARK OFFICE
CERTIFICATE OF CORRECTION

PATENT NO. : 7,648,681 B2  
APPLICATION NO. : 11/001623  
DATED : January 19, 2010  
INVENTOR(S) : Meyer et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1448 days.

Signed and Sealed this

Twenty-third Day of November, 2010

David J. Kappos  
*Director of the United States Patent and Trademark Office*